United States Patent [19]

Kettler et al.

[11] Patent Number: 4,907,158
[45] Date of Patent: Mar. 6, 1990

[54] METHOD FOR PERFORMING WORK ON CELLS OF A CELL CULTURE AND APPARATUS THEREFOR

[75] Inventors: Albrecht Kettler; Hubert Nasse; Walter Geis; Volker Wilke, all of Aalen; Wilhelm Ansorge, Gaiberg, all of Fed. Rep. of Germany

[73] Assignee: Carl-Zeiss-Stiftung, Heidenheim, Fed. Rep. of Germany

[21] Appl. No.: 198,294

[22] Filed: May 25, 1988

[30] Foreign Application Priority Data

May 29, 1987 [DE] Fed. Rep. of Germany ....... 3718066

[51] Int. Cl.⁴ .......................... G02B 21/32; G06K 9/00
[52] U.S. Cl. ............................. 364/413.01; 364/167.01
[58] Field of Search ............... 382/6; 364/413, 167.01, 364/188, 190, 413.13, 413.01, 413.07–413.11

[56] References Cited

U.S. PATENT DOCUMENTS

| | | | |
|---|---|---|---|
| 4,029,949 | 6/1977 | Dew | 364/167.01 |
| 4,245,298 | 1/1981 | Slater | 364/167.01 |
| 4,295,198 | 10/1981 | Copeland et al. | 382/6 |
| 4,413,314 | 11/1983 | Slater et al. | 364/188 |
| 4,453,266 | 6/1984 | Bacus | 382/6 |
| 4,563,744 | 1/1986 | Tsuboi | 364/167.01 |
| 4,577,141 | 3/1986 | Saiki et al. | 364/190 |
| 4,627,009 | 12/1986 | Holmes et al. | 364/167.01 |
| 4,660,148 | 4/1987 | Kishi et al. | 364/188 |
| 4,700,298 | 10/1987 | Palcic | 382/6 |
| 4,720,805 | 1/1988 | Vye | 364/190 |
| 4,741,043 | 4/1988 | Bacus | 382/6 |
| 4,757,437 | 7/1988 | Nishimura | 364/167.01 |

OTHER PUBLICATIONS

"Workplace for Microinjection into Living Cells", by Carl Zeiss.

Primary Examiner—Jerry Smith
Assistant Examiner—Gail O. Hayes
Attorney, Agent, or Firm—Walter Ottesen

[57] ABSTRACT

The invention is directed to a method for performing work on cells of a cell culture which includes microinjecting cells in the cell culture or drawing liquid from an individual cell or withdrawing whole cells with the aid of suction from the cell culture. The system is computer-supported and a marker movable in the image on a monitor is superposed on a television image of the cell culture. The marker is positioned in the television image on the cell to be injected by the operator by means of a relative movement of the marker with respect to the image. The coordinates of the cells marked in this way are stored by the computer which thereafter advances the capillary point automatically to the selected cells and penetrates the latter. Pursuant to a feature of an advantageous embodiment of the invention, the computer guides the penetration movement parallel to the longitudinal axis of the capillary by means of a superposed movement (k) of the object stage and through a superposed movement of the drive for the elevation displacement (z) of the capillary on the micromanipulator.

16 Claims, 3 Drawing Sheets

METHOD FOR PERFORMING WORK ON CELLS OF A CELL CULTURE AND APPARATUS THEREFOR

FIELD OF THE INVENTION

The invention relates to a method for performing work on cells of a cell culture such as making microinjections into the cells or making extractions from individual cells or withdrawing whole cells from the cell culture. A capillary is positioned relative to the cells which are observed under a microscope with a television camera connected thereto.

BACKGROUND OF THE INVENTION

Adding substances to living cells is significant for biological research as well as for gene technology. Various methods already exist for performing this work. The substance which is to be brought into the cells can first be placed in the medium surrounding the cells. The cell membrane must be penetrated so that the substance can get into the cells. This can take place by means of non-directed mechanical, electrical or chemical stimuli or by means of a laser beam which is focused on the cell.

All these methods have the disadvantage that the substance which is to be brought into the cell remains for the most part in the surrounding medium. Above all, it is not possible with the above-mentioned methods to deliver the substances only into the nucleus of a cell. For this reason, methods have been developed by means of which the substance is injected directly into the individual cells or cell nuclei with the aid of a glass capillary which is drawn out to a fine point at one end.

The publication entitled "Workplace for Microinjection into Living Cells" published by Carl Zeiss in the Federal Republic of Germany under publication number W41-131-e(XI-86) describes a system based on an inverted microscope. The inverted microscope has a stage on which a glass capillary is attached via a micromanipulator. The glass capillary is positioned so that it is inclined with respect to the optical axis of the microscope. The capillary can be purposefully moved in three axes in the culture vessel with the aid of the micromanipulator with the culture vessel being disposed on the stage of the microscope. The following individual steps are carried out for injection into the cells observed visually under the microscope: first the point of the capillary must be coarsely brought into the image field of the objective. Thereafter, the point of the capillary is positioned over the cell of interest by means of a movement of the micromanipulator (x, y). Finally, by means of a movement in the z-direction (that is, parallel to the optical axis of the microscope), the capillary point is brought into the cell and the injector is actuated and, after an adequate quantity of substance has been brought into the cell, the capillary is again lifted. In these steps, the injection does not occur in the direction of the axis of the capillary.

The above-described method is a purely manual method and requires several individual steps which are carried out precisely one after the other and for which some experience is necessary in order to correctly hit the cells and especially not to lower the capillary too far and thereby break the same. Furthermore, the penetration into the cells is not in the axial direction of the capillary so that the cell membrane is relatively seriously injured by means of the injection operation.

Another injection system is disclosed in the German patent publication No. DE-OS 35 11 700 which includes a capillary coupled to the focus drive of an inverted microscope and which is arranged in a vertical direction. In this system, the capillary must be first adjusted in the z-direction so that a movement of the capillary within the depth of field range of the microscope leads to a penetration into the cell. Thereafter, the cell into which the injection is to be made is driven with the aid of the mechanical stage beneath the point of the capillary which is only imprecisely recognizable. Thereafter, the actual injection operation is carried out in that the capillary is lowered with the aid of the focus drive and penetrates into the cell in the axial direction. After the injection is completed, the capillary is again lifted.

In this system, the danger is especially acute that the point of the capillary will break off or at least will become blocked when the point of the capillary reaches the base of the vessel since the capillary point comes into contact engagement with the base of the vessel in a direction perpendicular thereto. Furthermore, one easily loses the overview as to which cells have already been injected since the stage of the microscope is displaced with each injection whereby the image field continuously changes.

All this has as a consequence that with the known manual systems for cell injection, no more than approximately 300 cells can be injected in an hour, even by experienced personnel.

Furthermore, microbiological methods are known which provide for the drawing off of liquid from cells by suction or the drawing off by suction of entire cells from the cell culture. For this work, the capillary is used to penetrate into the cell or the capillary is positioned on the cell to be withdrawn by suction. In principle, with this method the same working steps are utilized as described above with respect to the example of the injection and the same limitations are present with respect to the speed with which the work can be performed.

SUMMARY OF THE INVENTION

It is an object of the invention to provide a method for working on cells of cell cultures which permits work to be performed more reliably and faster than permitted by the known methods. The work performed on the cells includes injecting the cells or drawing off substances via suction from individual cells or drawing off entire cells from a cell culture via suction. The method of the invention for working on cells in a cell culture includes positioning a capillary relative to the cells which are observed under a microscope with a television camera connected thereto. It is also an object of the invention to provide an apparatus for carrying out the method.

The method according to a preferred embodiment of the invention includes the steps of: providing a capillary in the region of the cells of the cell culture; observing a television image of the cells on a television monitor obtained from the microscope to which a television camera is connected; superposing a marking on the television image; positioning the marking in the television image on the cells selected to be worked upon by means of a relative movement between the latter and the marking and storing the image coordinates of the marked cells in a computer; converting the image coordinates into object coordinates of a positioning system for positioning the capillary and the stage; and, performing the required work on the selected cells by a computer-controlled positioning of the capillary relative to the selected cells and to the object coordinates.

With the method of the invention, a computer controls the positioning and the penetration of the capillary into the cell. Since this critical moving operation now occurs automatically, a higher working speed is obtained and the danger that the capillary breaks off because of an erroneous actuation is greatly reduced. The operator must now only mark the cells in the monitor image which are to be injected or to be drawn off by suction. In an advantageous further embodiment of the invention, it is even possible to conduct this operation by means of an image analysis system which automatically recognizes specific cell types or cells in a specific stage of development by their geometric form.

The method according to the invention assures a uniform depth of the penetrating movement into the cell and therefore provides reproducible results with respect to the nature and magnitude of the cell injury than the previous manually controlled method. Furthermore, the duration that the capillary remains in the cell and therefore the injected or drawn off volume are precisely determinable in advance and are reproducible.

With the aid of the computer, it is further possible to store the coordinates of all cells which have already been processed. In this way, the user can at any time inform himself as to which and how many cells he has already treated. It is then also possible to interrupt the operation at any time and to continue the operation at a later point in time at precisely the same location. Furthermore, the effect of the injection can for example be controlled by comparing the development of the cells into which an injection has been made with cells into which no injection has been made over a longer period of time. This possibility becomes available in an advantageous manner in that the cells are located in a vessel which is provided with reference marks and the coordinates of the injected cells together with those of the reference marks are stored so that a reliable relocation of individual cells is assured even after an exchange of the specimen vessel.

A separate drive can be provided for the penetration movement of the capillary in the axial direction. Since the computer coordinates several movements with one another in a way that is hardly possible with a manual control, this penetration movement in the capillary direction can, however, be carried out without the necessity of providing a separate drive in the axial direction of the capillary. The computer control can put together the desired movement operation by superposing the displacement of the microscope stage and the downward displacement in the z-direction of the manipulator.

It is furthermore advantageous if the entire specimen region is subdivided into several mutually adjoining fields which can be sequentially accessed by the computer control. The corresponding image fields provided with an identification character can then be systematically and sequentially processed by the user. In this way, multiple injections into cells or the omission of cells is reliably prevented.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
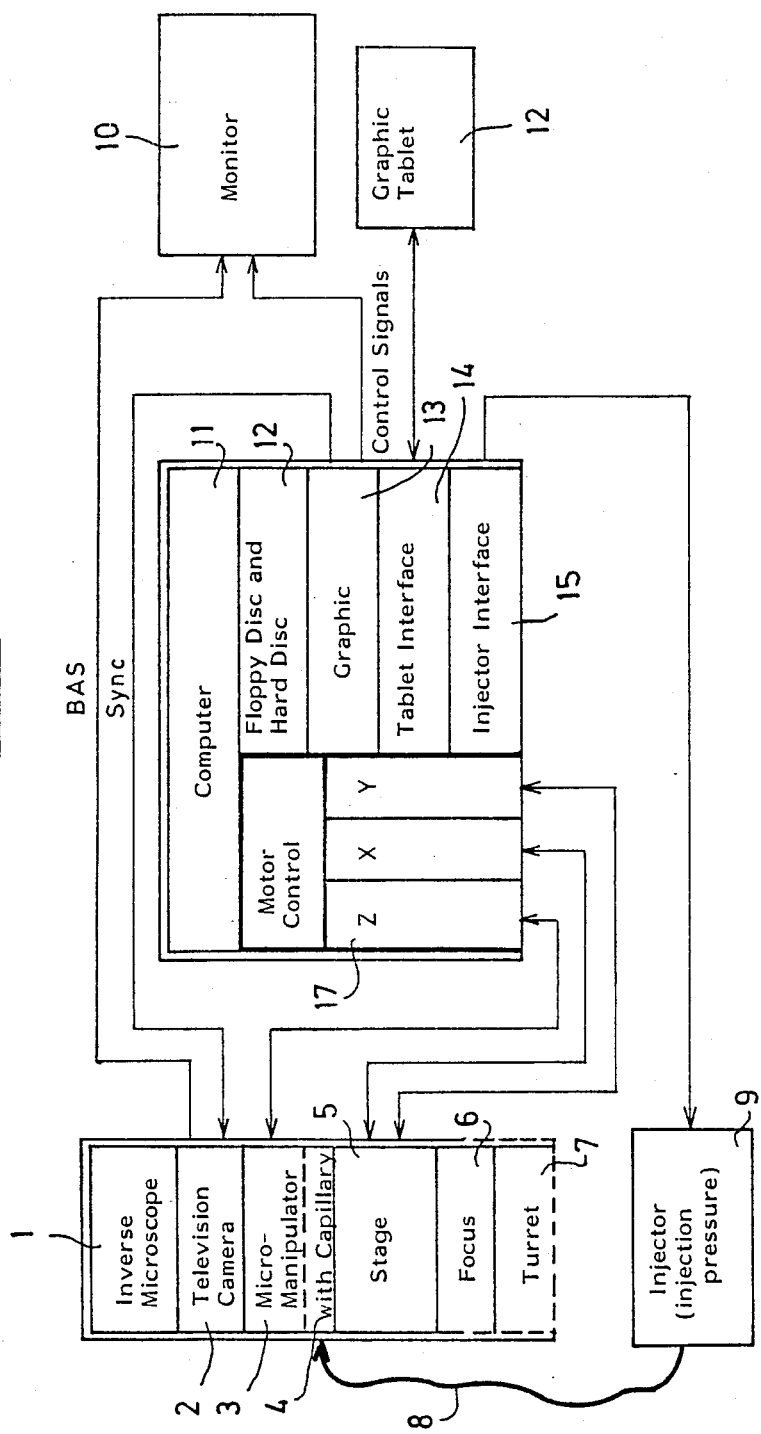
FIG. 1 is a block diagram which shows the interconnection of the individual components of an embodiment of the workplace apparatus of the invention for carrying out the method according to an embodiment of the invention.

The system shown in the block diagram of FIG. 1 for injecting cells builds upon an inverted microscope which has for this purpose a condenser with a long focal length and is provided with exchangeable equipment (not shown) for various optical contrasting methods such as phase contrast and differential-interference contrast. The microscope 1 has a turret 7 for objectives of different magnifications.

A scanning stage which is motor-drivable in two coordinates (x, y) is located above the objective turret 7. The scanning table usually has a step resolution of 0.25 $\mu$m and can be moved with a selectable speed. As shown in the perspective view of FIG. 2, the stage 5 supports a holder for the specimen vessel 18 containing the cells to be injected.

A television camera 2 and the micromanipulator 3 for holding the injection capillary 4 are both attached to the microscope 1. An enlarged image of the cell cultures to be treated can be made visible on the monitor 10 with the aid of this television camera.

The capillary 4 is connected to an injector 9 via a flexible pressure tube 8 which effects an outward flow of the injection liquid from the capillary and makes possible an adjustment of the holding pressure, the injection pressure and the flushing pressure.

The above-mentioned components are also available in known systems recited above as being of the state of the art and are therefore not described here in greater detail.

As mentioned above, the stage 5 of the microscope is movable with the aid of a motor. The two drives for the movement of the stage in the x-direction and in the y-direction are identified by reference numerals 19 and 20, respectively, in the detail perspective view of FIG. 2. The micromanipulator 3 can likewise be displaced via a motor drive 21 but in the z-direction. Furthermore, the holder 27 of the micromanipulator to which the capillary 4 is attached has displacement possibilities for a movement in the x-direction and y-direction. In the embodiment described, manually actuable adjusting knobs (24 and 26) are provided; however, it is also possible to provide motorized drives for these movements.

The capillary 4 dips at an angle into the specimen vessel 18 on the stage 5 of the microscope 1 with the angle of inclination of the capillary to the plane of the stage being adjustable by pivoting the holder 27 of the capillary about the axis 29.

Figure 2:
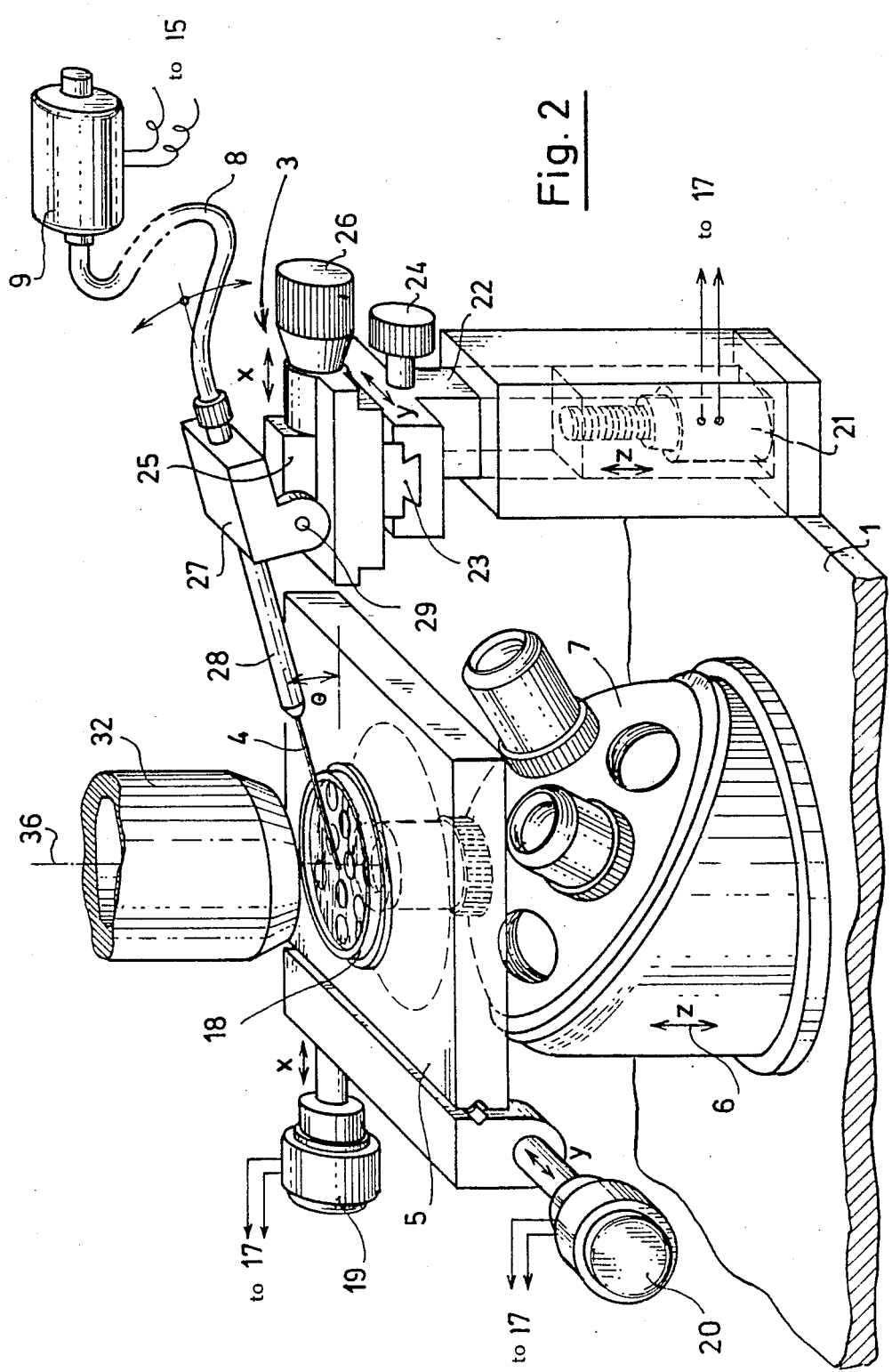
FIG. 2 is a perspective schematic of the movable parts of the injection system on the inverted microscope of the apparatus shown, in FIG. 1.

The configuration of the positioning system for the capillary 4 and for the specimen vessel 18 shown in FIG. 2 is known with respect to its components.

According to a feature of the invention, the drives (19 and 20) of the scanning stage 5 and the drive 21 for the z-movement of the micromanipulator are connected to the motor control of the computer identified in FIG. 1 by reference numeral 11. This computer 11 can, for example, be a personal computer having the capability of graphic display such as the IBM PC/XT. The graphic card 13 of the computer 11 is likewise connected to the monitor 10. Furthermore, the television camera 2 on the microscope 1 is externally synchronized by means of synchronizing pulses of the graphic card. The monitor 10 contains a mixing stage in which the symbols generated by the graphic card 13 are superposed on the video signal of the television camera 2.

In addition, a graphic tablet 12 is connected to the computer 11. With the aid of the graphic tablet 12, the user can displace the marks generated by the graphic card on the image of the monitor 10 as will be described below. In lieu of the graphic tablet, a mouse, a so-called trackball or a joy stick can be used for controlling the movement of the marks.

In addition, the control computer 11 is connected via an injector interface 15 to the injecting unit 9 for the capillary 4 and, among other things, controls the injection time and therefore the quantity of the liquid to be injected into the cells. Via the interface 15, the injection pressure can also be controlled in dependence upon time in correspondence to the movement operation which the capillary 4 carries out. For example, a slight overpressure is adjusted before the injection in order to prevent a return flow of liquid in the capillary. During the penetration movement, the injection pressure is increased in order to prevent a blockage of the capillary and then the actual injection pressure is adjusted.

The microinjection is conducted with the aid of the system described above in the manner described below.

Preparatory Work

Figure 4:
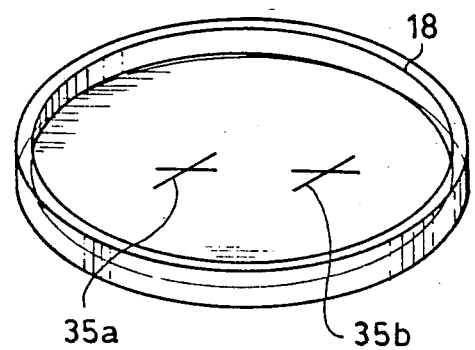
FIG. 4 is an enlarged perspective view of the specimen vessel shown on the stage of the inverted microscope of FIG. 2.

The cell vessel 18 is secured to the microscope stage 5. Two reference marks (35a, 35b) are applied at the base of the vessel shown as an example in FIG. 4. With the aid of these reference marks, the vessel 18 is so aligned that these marks lie in approximately the x-direction of the stage. The reference marks furthermore define the origin of the image coordinate system in a definite manner and permit the cells to be located again in the vessel 18. Furthermore, it can be advantageous to inscribe a uniform pattern in the base of the cell vessel in order to mark mutually adjoining fields.

Thereafter, the capillary is filled with injection liquid and clamped into the capillary holder 27. Then, by means of a manual (x, y)-displacement effected with the aid of rotatable knobs (24 and 26), the capillary is brought into the image field under the condenser 32 approximately on the axis 36 of the microscope.

The desired injection pressure or holding pressure at the injector 9 is adjusted in the event that the control of the pressure does not take place via the computer.

Data Input

Figure 3:
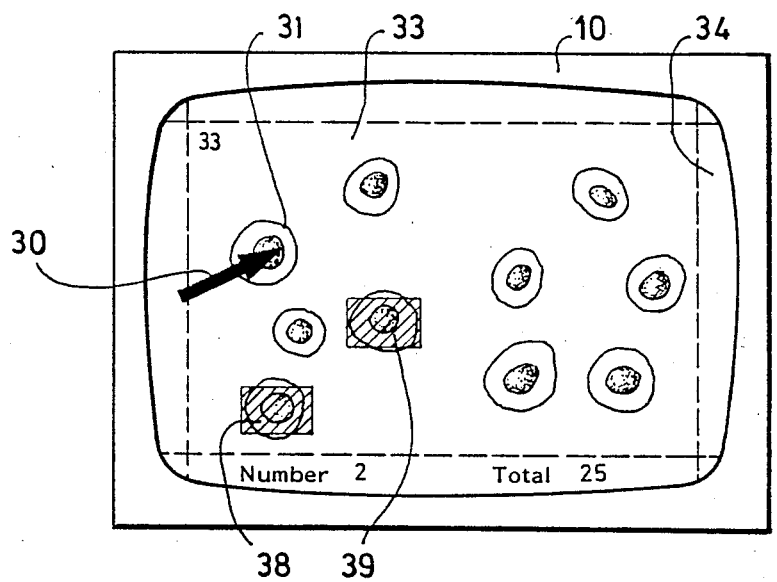
FIG. 3 shows the image on the monitor of FIG. 1.

Thereafter, the program for controlling the working sequence is called up in the computer 11. This program requires the input of several parameters necessary to carry out the program, namely: the magnification of the objective utilized and the injection angle $\theta$ at which the capillary 4 is inclined with respect to the surface of the stage. Furthermore, it is possible to select a plurality of mutually adjoining fields which the motor-driven stage 5 accesses sequentially under the control of the computer. The corresponding image fields (33, 34) are then provided with an enclosed border generated by the graphic card 13 as illustrated in FIG. 3 and with an identification number 33 and displayed on the monitor 10. At this position, the injection modus can be selected such as the continuous outflow of the injection liquid from the capillary or the outflow only after penetration of the capillary into a cell or the desired pressure course can be provided. It is furthermore possible to select the speed of the penetration movement. For example, a higher speed is needed for cells having a more yieldable cell membrane than for cells having a relatively hard cell membrane.

Vessel Position

The data is inputted under the control of the menu by utilizing the graphic tablet 12 and the screen of the monitor 10. After the data has been inputted, the image generated by the microscope is called up on the image screen 10 and then focussed onto the vessel base and the two reference marks on the vessel base are accessed. In this connection, the graphic tablet serves to control the stage position above the objective of the microscope.

The reference marks on the base of the vessel are then marked with an arrow-shaped cursor 30 shown in FIG. 3 thereby bringing the respective positions of the vessel marks into correspondence with the coordinate system of the computer. If the computer already recognizes the approximate positions of the markings, the computer itself can drive the markings into the image field of the television camera and the operator only has to mark the exact position of the marks on the base of the vessel with the cursor 30. The computer can already recognize the approximate position of the markings, for example, when utilizing standardized vessels or when continuing an interrupted injection without the vessel having been removed from the stage.

Capillary Adjustment and Test Injection

After a correct placement of the vessel, a focussing on the capillary point takes place with the focussing drive and the capillary point is brought approximately into the center of the field of view of the microscope with the aid of the x/y-displacement unit (24, 26) of the micromanipulator 3. Thereafter, the plane of the cells at the base of the vessel is focused upon.

The capillary is then interactively lowered under the control of the graphic tablet 12 until the point of the capillary 4 penetrates into the cells. This position is transferred to the computer so that the latter now has an information concerning the extent of the z-movement for later automatic injection. The position of the point of the capillary in the xy-plane in the image coordinate system is provided to the computer in that the cursor 30 is positioned with its point on the point of the capillary.

A cell is now selected on the image screen into which a test injection is to be carried out in that this cell is likewise marked with the cursor 30. After this marking, the computer moves the capillary point automatically into the marked position and penetrates the cell. In the event that the capillary does not penetrate far enough into the cell, it is again lowered until the test injection is successful. A correction of the values determined during the adjustment operation for the z-downward movement takes place at this time.

In the course of the test injection, the dwell time of the capillary in the cell which is to be maintained by the computer as well as the injection pressure can be checked and modified if required. If the test injection is run through successfully, the actual routine injections can be done.

Marking of the Cells of an Image Field

For this purpose and with the aid of the graphic tablet 12, the image screen cursor marker 30 is sequentially positioned on the selected cells which are to be injected. The coordinates of these cells in the image screen coordinate system are transferred in each instance to the computer by pressing a key and are then stored there. The computer administrates the coordinates of the marked cells and continuously shows the number of cells marked in the image field as well as the total number of cells marked. Furthermore, a quadrilaterally-shaped marking field is superposed on the image of each marked cell by means of which the marked cells are characterized. Two marking fields are shown in FIG. 3 and are identified therein by reference numerals 38 and 39.

It is also possible to detect the coordinates of the selected cells in that these cells are brought sequentially under the cursor marker 30 by movement of the stage 5. The cursor marker 30 is fixed, for example, in the center of the image. The stage coordinates are then transferred to the computer by pressing a key.

If a marking is set in error, it is possible to again erase the set marking and in this way prevent the cell from being accessed by the automatic injection which follows.

Injection of the Marked Cells

The injection operation is controlled by the computer and can, however, be interrupted at any time by the operator, for example, in the event that the capillary becomes blocked. In the course of the automatic injection operation, the computer transforms the image field coordinates of the marked cells into the coordinate values of the handling system necessary for controlling the stage 5 and the z-drive 21 of the micromanipulator 3. Thereafter, the computer drives the capillary point relative to the marked cells and positions the capillary point in the cells in that the computer penetrates the cells by means of a movement with the point of the capillary. This movement is put together in correspondence with the inputted angle for the inclination of the capillary. The valve of the injector 9 is opened during the preset time and then the capillary is withdrawn and driven to the next marked cell.

It is also possible to effect a penetration of the cells by means of a drive which moves the capillary 4 in the axial direction. Such a drive can include a motor mounted in the capillary holder 27 which is driven by the computer 11 as soon as the point of the capillary reaches a predetermined position with reference to the cell to be treated.

Going to the next Image Field

If it was initially defined how many image fields are to be processed in the x-direction and in the y-direction, the next image field which follows directly after the previous ones is then automatically accessed. If no definition is available or if all defined fields have been already processed, the next image field is then selected by the operator. For this purpose, the stage can be freely driven or the table can be driven precisely one image field in the x-direction or in the y-direction. The instantaneous position within the image field raster is indicated by means an identification number 33. If one arrives at an image field when driving the stage in which a cell has already been injected, this will likewise be provided on the monitor screen with a marking field in order to reliably prevent multiple injections.

The last three steps of: (1) marking the cells with the cursor by the operator; (2) injection into the marked cells under computer control; and, (3) automatic accessing of the next field; are repeated until the desired number of cells have been injected or all defined image fields have been sequentially processed.

If the injection must be prematurely interrupted for any reason, the injection can be continued at any desired point in time at the correct location even if the cell vessel is taken out of the holder on the microscope stage 5 in the meantime. It is then only necessary that the image coordinate system be again connected to the reference marks as described in the description appearing above under the heading "Vessel Position".

Since the cell coordinates can, if desired, be also permanently stored, one can again specifically access all fields in which cells have been injected at a later point in time. In this way, the possibility is afforded to follow the development of these cells in comparison to those which have not been injected.

Geometric Calibration

A geometric calibration is only necessary when the system is first taken into use. The geometric calibration serves to permit the actual position of a cell on the microscope stage to be computed from the position of the cell on the monitor. Since the imaging magnifications of all exchangeable objectives are included in the conversion, the monitor coordinates for each objective must be calibrated in units of the stage coordinates.

For this purpose, a well recognized object is displaced on the monitor 10 in the x-direction and y-direction by moving the microscope stage. The particular monitor position is transmitted to the computer by the marking of the object on the image screen of the monitor 10 with the point of the cursor marker 30. The computer determines the calibration factors in the x-direction and y-direction from the corresponding coordinate position and monitor position. These calibration factors corresponding to the individual objectives are permanently stored in the computer 11.

Further Embodiments of the System

As described under the heading "Data Input" above, the computer is advised as to the objective used before the actual injection. This operation can be further simplified by utilizing a motorized objective turret and assigning a code readable by the computer to the turret positions or to the objectives connected thereto. In this way, the manual input of the objective utilized by the operator is then no longer needed.

In the system described above, the marking of the cells of an image field is performed manually in that the mark is set upon the cells of interest by the operator with the aid of a visual observation. This operation can be performed automatically in that the selection of the cells of interest and the determination of the cell coordinates can be performed by means of center-of-gravity formation with the aid of an image-analyzing system.

Furthermore, the system described is not only for injecting liquid into cells; instead, it is also suitable for withdrawing liquid from a cell by means of suction or for withdrawing entire cells by means of suction from a cell culture.

Finally, the first part of the method up to marking of the cells of interest and the storage of their coordinates relative to the reference marks on the base of the cell is also suitable for marking living cells whose development (growth, movement, morphological changes et cetera) is to be followed over a longer period of time without injecting into the cells or drawing liquid therefrom.

With the system described above for the computer-supported microinjection, a significantly greater number of cells per unit of time can be injected than with the systems of the prior art initially described above. It has been shown that it is possible to inject 1,500 cells per hour which is a rate faster by a factor of five than with known methods. This is not only effected by the possibility of the fast positioning of a cursor marker on an image screen in comparison to the sensitive positioning of the capillary itself in the vessel; instead, it is also owing to the condition that a break of the capillary occurs less frequently as does the time-consuming exchange and readjustment thereof associated with such a breakage. The latter condition is brought about by the reliable computer control of the penetration movement and of the injection pressure.

It is understood that the foregoing description is that of the preferred embodiments of the invention and that various changes and modifications may be made thereto without departing from the spirit and scope of the invention as defined in the appended claims.

What is claimed is:

1. A method of performing work on cells of a cell culture with the aid of a capillary, the work on the cells including any one of the following: microinjecting the cells or drawing substances out of cells with the aid of suction or drawing entire cells out of the cell culture with the aid of suction; the cells being mounted on the stage of a microscope for observing the cells, the method comprising the steps of:
   providing a capillary in the region of the cells of the cell culture;
   observing a television image of the cells on a television monitor obtained from the microscope to which a television camera is connected;
   superposing a marking on the television image;
   positioning the marking in the television image on the cells selected to be worked upon by means of a relative movement between the latter and said marking and storing the image coordinates of the marked cells in a computer;
   converting the image coordinates into object coordinates of a positioning system for positioning the capillary and the stage; and,
   performing the required work on the selected cells by a computer-controlled positioning of the capillary relative to the selected cells and to the object coordinates.

2. The method of claim 1, wherein the selected cells are microinjected and the injection movement of the capillary in the capillary direction is caused by a superposed movement of the positioning system of the capillary and the stage in two coordinates in correspondence with the angle of inclination $\theta$ of the capillary with respect to the stage.

3. The method of claim 1, wherein the specimen region is subdivided into several mutually adjoining image fields of a fixed size with the boundaries of the image fields being superposed upon the television image and with each of the image fields being provided with an identification character.

4. The method of claim 1, wherein the cells of the cell culture are disposed in a vessel having reference marks thereon which are visible in the television image and wherein the method includes the further step of bringing the image coordinates into correspondence with the reference marks by means of a calibration operation.

5. The method of claim 1, wherein the cells of the cell culture are disposed in a vessel having reference marks thereon and wherein the coordinates of the selected cells are permanently stored together with an identification code number and the coordinates of said reference marks after the selected cells have been treated.

6. The method of claim 1, wherein a test operation is carried out manually in advance of the computer-controlled work on the selected cells with the coordinates of the point of the capillary and of the particular cell to be worked upon being brought into correspondence with each other and taken over by the computer.

7. The method of claim 1, wherein the control by the computer of the work to be performed on the selected cells such as the control of the duration of injection, quantity of injected cells or quantity drawn off by suction is performed in correspondence to predetermined values.

8. The method of claim 1, wherein the selected cells are microinjected and wherein the speed of the injection movement of the capillary into a cell is selectable.

9. The method of claim 1, wherein the selected cells are microinjected and wherein the course of the pressure of the microinjection as a function of time is controlled by the computer in correspondence to the movement operation of the capillary.

10. The method of claim 1, wherein work performed on the selected cells is selected by means of an image analysis system.

11. An apparatus for performing work on cells of a cell culture, the work on the cells including any one of the following: microinjecting the cells or drawing substances out of cells with the aid of suction or drawing entire cells out of the cell culture with the aid of suction; the apparatus comprising:
   a microscope for forming a microscope image of the cells, the microscope defining an optical axis and including: an object stage movable in at least two directions and adapted for receiving the cell culture thereon; and, stage positioning means for positioning said stage in said directions;
   capillary means for performing the work on selected cells of the cell culture;
   a television arrangement including a television monitor for showing said microscope image thereon;
   a computer having a graphics capability;
   a memory connected to said computer;
   graphic means for providing graphic symbols and a graphic marker;
   said graphic means including superposing means for superposing the graphic symbols on said monitor;
   said graphic means also including interface means for placing a graphic marker on said monitor;
   micromanipulator means for accommodating said capillary means;
   micromanipulator positioning means for positioning said micromanipulator in at least one direction; and,
   computer program means for converting image coordinates determined by said graphic means into object coordinates and for controlling said stage positioning means and said micromanipulator positioning means via said computer.

12. The apparatus of claim 11, comprising a specimen vessel for accommodating the cell culture therein; and, said specimen vessel having viewable markings thereon which serve to detect the position of said vessel on said stage.

13. The apparatus of claim 11, wherein said capillary means comprises an injection unit for injecting the selected cells and a capillary; and, adjusting means for adjusting the angle $\theta$ of said capillary relative to said optical axis of said microscope.

14. The apparatus of claim 11, wherein said capillary means comprises an injection unit for injecting the selected cells and a capillary; and, drive means for imparting an axial movement to said capillary.

15. The apparatus of claim 11, connecting means for connecting said computer to said stage positioning means and said micromanipulator positioning means for computer-controlling the positioning of said stage and said micromanipulator means.

16. The apparatus of claim 11, comprising computer program means for storing several sets of image coordinates and corresponding sets of object coordinates computed therefrom via said graphic means.

* * * * *